United States Patent [19]

Wiezer et al.

[11] 4,340,534
[45] Jul. 20, 1982

[54] ETHERS BASED ON POLYALKYL-1-OXADIAZASPIRODECANES

[75] Inventors: Hartmut Wiezer, Gersthofen; Gerhard Pfahler, Augsburg, both of Fed. Rep. of Germany

[73] Assignee: Hoechst Aktiengesellschaft, Fed. Rep. of Germany

[21] Appl. No.: 194,140

[22] Filed: Oct. 6, 1980

[30] Foreign Application Priority Data

Oct. 10, 1979 [DE] Fed. Rep. of Germany ....... 2941004

[51] Int. Cl.³ .................... C08G 65/22; C08K 5/35; C07D 471/10; C08L 23/12
[52] U.S. Cl. .................................. 524/99; 525/187; 525/403; 525/405; 525/407; 528/367; 546/19; 525/408; 524/102
[58] Field of Search ................. 260/45.8 NZ; 525/187, 525/403, 405, 407, 408; 528/367; 546/19

[56] References Cited

U.S. PATENT DOCUMENTS 4,066,615 1/1978 Murayama et al. ......... 260/45.8 NT
4,107,139 8/1978 Mayer et al. ............... 260/45.8 NZ
4,110,334 8/1978 Mayer et al. ............ 260/45.8 NZ X
4,118,369 10/1978 Minagawa et al. ............ 260/45.8 N
4,263,505 4/1981 Slongo et al. ............... 260/45.8 NZ Primary Examiner—Earl A. Nielsen
Attorney, Agent, or Firm—Connolly and Hutz

[57] ABSTRACT

The invention relates to epoxy compounds which can be polymerized to give polyethers and which are formed from polyalkyl-1-oxadiazaspirodecanes of the formula

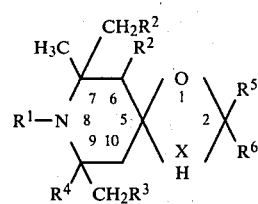

in which X is a group

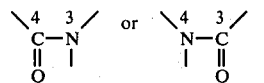

and an epihalogenohydrin by linking the nitrogen atom of the 5-membered ring to the 2,3-epoxypropyl radical. Polyethers which have degrees of polymerization of up to approx. 50 and which exhibit a very low volatility and are suitable as light stabilizers for organic polymers can be obtained by heating the epoxides.

13 Claims, No Drawings

ETHERS BASED ON POLYALKYL-1-OXADIAZASPIRODECANES

The invention relates to new ethers or polyethers based on polyalkyldiazaspirodecanes, to a process for their manufacture and to their use as high-grade light stabilizers for stabilizing organic polymers against photo-oxidation.

The new compounds possess the general formula (I)

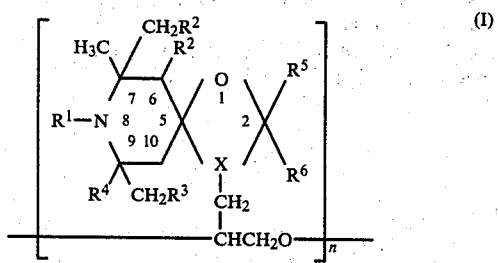

in which n is an integer from 1 to 50, preferably from 1 to 20 and especially from 2 to 15, and, in the event that n=1, an oxirane ring is completed via the free bonds, X denotes a group of the formula (II) or (III)

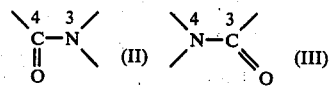

wherein the indices 3 and 4 indicate the ring positions in the diazaspirodecane system and one bond of the nitrogen is attached to a $CH_2$ group of the ether radical, $R^1$ is hydrogen, oxygen or $C_1$- to $C_{12}$-alkyl, preferably hydrogen, oxygen or $C_1$- to $C_4$-alkyl and especially hydrogen, $R^2$ and $R^3$ are either identical and denote hydrogen or a $C_1$- to $C_5$-alkyl group, preferably hydrogen or a methyl group and especially hydrogen, in which case $R^4$ is a methyl group, or $R^2$ is hydrogen or $C_1$- to $C_5$-alkyl and $R^3$ and $R^4$, conjointly with the carbon atoms to which they are linked, represent a $C_5$- or $C_6$-cycloalkyl group or a group of the formula

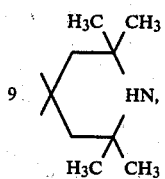

$R^5$ represents hydrogen, $C_1$- to $C_{30}$-alkyl, preferably $C_1$- to $C_{18}$-alkyl and especially $C_1$- to $C_5$-alkyl, a phenyl or naphthyl group which is unsubstituted or substituted by chlorine or $C_1$- to $C_4$-alkyl, preferably the former, or a $C_7$- to $C_{12}$-phenylalkyl group, preferably a benzyl group, which is unsubstituted or substituted by $C_1$- to $C_4$-alkyl, $R^6$ is hydrogen, $C_1$- to $C_{30}$-alkyl, preferably $C_1$- to $C_{18}$-alkyl and especially $C_1$- to $C_{13}$-alkyl, a phenyl or naphthyl group, preferably a phenyl group, which is unsubstituted or substituted by chlorine or $C_1$- to $C_4$-alkyl, or a $C_7$- to $C_{12}$-phenylalkyl group, preferably a benzyl group, which is unsubstituted or substituted by $C_1$- to $C_4$-alkyl, or $R^5$ and $R^6$, conjointly with the carbon atom which is linked to them, denote a $C_5$- to $C_{18}$-, preferably $C_5$- to $C_{12}$-, cycloalkyl group which is unsubstituted or substituted by up to four $C_1$- to $C_4$-alkyl groups, preferably methyl groups, or denote a group of the formula

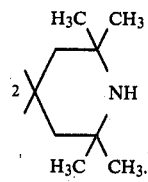

The following are examples of ether derivatives, according to the invention, of the formula (I) which have n=1 and from which the oligoethers and polyethers can be obtained:

(1) 2,2,7,7,9,9-hexamethyl-3-(2,3-epoxypropyl)-1-oxa-3,8-diaza-4-oxospiro-(4,5)-decane
(2) 2,2,7,7,9,9-hexamethyl-4-(2,3-epoxypropyl)-1-oxa-3-oxo-4,8-diazaspiro-(4,5)-decane
(3) 2,2,7,7,8,9,9-heptamethyl-3-(2,3-epoxypropyl)-1-oxa-3,8-diaza-4-oxospiro-(4,5)-decane
(4) 2,2,7,7,8,9,9-heptamethyl-4-(2,3-epoxypropyl)-1-oxa-3-oxo-4,8-diazaspiro-(4,5)-decane
(5) 2,7,7,9,9-pentamethyl-2-ethyl-3-(2,3-epoxypropyl)-1-oxa-3,8-diaza-4-oxospiro-(4,5)-decane
(6) 2,7,7,9,9-pentamethyl-2-propyl-3-(2,3-epoxypropyl)-1-oxa-3,8-diaza-4-oxospiro-(4,5)-decane
(7) 2,7,7,9,9-pentamethyl-2-isopropyl-3-(2,3-epoxypropyl)-1-oxa-3,8-diaza-4-oxospiro-(4,5)-decane
(8) 2,7,7,9,9-pentamethyl-2-butyl-3-(2,3-epoxypropyl)-1-oxa-3,8-diaza-4-oxospiro-(4,5)-decane
(9) 2,7,7,9,9-pentamethyl-2-sec.-butyl-3-(2,3-epoxypropyl)-1-oxa-3,8-diaza-4-oxospiro-(4,5)-decane
(10) 2,7,7,9,9-pentamethyl-2-pentyl-3-(2,3-epoxypropyl)-1-oxa-3,8-diaza-4-oxospiro-(4,5)-decane
(11) 2,7,7,9,9-pentamethyl-2-hexyl-3-(2,3-epoxypropyl)-1-oxa-3,8-diaza-4-oxospiro-(4,5)-decane
(12) 2,7,7,9,9-pentamethyl-2-(3-methylbutyl)-3-(2,3-epoxypropyl)-1-oxa-3,8-diaza-4-oxospiro-(4,5)-decane
(13) 7,7,9,9-pentamethyl-2-ethyl-2-(2-methylbutyl)-3-(2,3-epoxypropyl)-1-oxa-3,8-diaza-4-oxospiro-(4,5)-decane
(14) 2,7,7,9,9-pentamethyl-2-heptyl-3-(2,3-epoxypropyl)-1-oxa-3,8-diaza-4-oxospiro-(4,5)-decane
(15) 2,7,7,9,9-pentamethyl-2-octyl-3-(2,3-epoxypropyl)-1oxa-3,8-diaza-4-oxospiro-(4,5)-decane
(16) 2,7,7,9,9-pentamethyl-2-nonyl-3-(2,3-epoxypropyl)-1-oxa-3,8-diaza-4-oxospiro-(4,5)-decane
(17) 2,7,7,9,9-pentamethyl-2-undecyl-3-(2,3-epoxypropyl)-1-oxa-3,8-diaza-4-oxospiro-(4,5)-decane
(18) 2,7,7,9,9-pentamethyl-2-octadecyl-3-(2,3-epoxypropyl)-1-oxa-3,8-diaza-4-oxospiro-(4,5)-decane
(19) 2,7,7,9,9-pentamethyl-2-benzyl-3-(2,3-epoxypropyl)-1-oxa-3,8-diaza-4-oxospiro-(4,5)-decane
(20) 2,7,7,9,9-pentamethyl-2-(2-phenylethyl)-3-(2,3-epoxypropyl)-1-oxa-3,8-diaza-4-oxospiro-(4,5)-decane
(21) 7,7,9,9-tetramethyl-2,2-diethyl-3-(2,3-epoxypropyl)-1-oxa-3,8-diaza-4-oxospiro-(4,5)-decane
(22) 7,7,9,9-tetramethyl-2-ethyl-2-propyl-3-(2,3-epoxypropyl)-1-oxa-3,8-diaza-4-oxospiro-(4,5)-decane
(23) 7,7,9,9-tetramethyl-2-ethyl-2-butyl-3-(2,3-epoxypropyl)-1-oxa-3,8-diaza-4-oxospiro-(4,5)-decane
(24) 7,7,9,9-tetramethyl-2-ethyl-2-pentyl-3-(2,3-epoxypropyl)-1-oxa-3,8-diaza-4-oxospiro-(4,5)-decane

(25) 7,7,9,9-tetramethyl-2,8-dipropyl-3-(2,3-epoxypropyl)-1-oxa-3,8-diaza-4-oxospiro-(4,5)-decane
(26) 7,7,9,9-tetramethyl-2,2-dibutyl-3-(2,3-epoxypropyl)-1-oxa-3,8-diaza-4-oxospiro-(4,5)-decane
(27) 7,7,9,9-tetramethyl-2,2-dipentyl-3-(2,3-epoxypropyl)-1-oxa-3,8-diaza-4-oxospiro-(4,5)-decane
(28) 7,7,9,9-tetramethyl-2,2-diheptyl-3-(2,3-epoxypropyl)-1-oxa-3,8-diaza-4-oxospiro-(4,5)-decane
(29) 7,7,9,9-tetramethyl-2,2-dibenzyl-3-(2,3-epoxypropyl)-1-oxa-3,8-diaza-4-oxospiro-(4,5)-decane
(30) 2,7,7,9,9-pentamethyl-2-(2-methyl-2-phenylpropyl)-3-(2,3-epoxypropyl)-1-oxa-3,8-diaza-4-oxospiro-(4,5)-decane
(31) 7,7,9,9-tetramethyl-2-methyl-3-(2,3-epoxypropyl)-1-oxa-3,8-diaza-4-oxospiro-(4,5)-decane
(32) 7,7,9,9-tetramethyl-2-butyl-3-(2,3-epoxypropyl)-1-oxa-3,8-diaza-4-oxospiro-(4,5)-decane
(33) 7,7,9,9-tetramethyl-2-isopentyl-3-(2,3-epoxypropyl)-1-oxa-3,8-diaza-4-oxospiro-(4,5)-decane
(34) 7,7,9,9-tetramethyl-2-isoheptyl-3-(2,3-epoxypropyl)-1-oxa-3,8-diaza-4-oxospiro-(4,5)-decane
(35) 7,7,9,9-tetramethyl-2-isooctyl-3-(2,3-epoxypropyl)-1-oxa-3,8-diaza-4-oxospiro-(4,5)-decane
(36) 7,7,9,9-tetramethyl-2-isononyl-3-(2,3-epoxypropyl)-1-oxa-3,8-diaza-4-oxospiro-(4,5)-decane
(37) 2,2,4,4-tetramethyl-7-oxa-3,13-diaza-13-(2,3-epoxypropyl)-14-oxodispiro-(5,1,4,2)-tetradecane
(38) 2,2,4,4-tetramethyl-7-oxa-3,13-diaza-10-tert.-butyl-13-(2,3-epoxypropyl)-14-oxodispiro-(5,1,4,2)-tetradecane
(39) 2,2,4,4-tetramethyl-7-oxa-3,14-diaza-14-(2,3-epoxypropyl)-15-oxodispiro-(5,1,5,2)-pentadecane
(40) 2,2,4,4,10,12-hexamethyl-7-oxa-3,14-diaza-14(2,3-epoxypropyl)-15-oxodispiro-(5,1,5,2)-pentadecane
(41) 2,2,4,4,10,10,12-heptamethyl-7-oxa-3,14-diaza-14-(2,3-epoxypropyl)-15-oxodispiro-(5,1,5,2)-pentadecane
(42) 2,2,4,4,10,10,12,12-octamethyl-7-oxa-3,14-diaza-14-(2,3-epoxypropyl)-15-oxodispiro-(5,1,5,2)-pentadecane
(43) 2,2,4,4-tetramethyl-7-oxa-3,20-diaza-20-(2,3-epoxypropyl)-21-oxodispiro-(5,1,11,2)-heneicosane
(44) 2,7,7,9,9-pentamethyl-2-ethyl-1-oxa-3-oxo-4-(2,3-epoxypropyl)-4,8-diazaspiro-(4,5)-decane
(45) 2,7,7,9,9-pentamethyl-2-hexyl-1-oxa-3-oxo-4-(2,3-epoxypropyl)-4,8-diazaspiro-(4,5)-decane
(46) 2,7,7,9,9-pentamethyl-2-undecyl-1-oxa-3-oxo-4-(2,3-epoxypropyl)-4,8-diazaspiro-(4,5)-decane
(47) 7,7,9,9-tetramethyl-2,2-diethyl-1-oxa-3-oxo-4-(2,3-epoxypropyl)-4,8-diazaspiro-(4,5)-decane
(48) 7,7,9,9-tetramethyl-2,2-dibutyl-1-oxa-3-oxo-4-(2,3-epoxypropyl)-4,8-diazaspiro-(4,5)-decane
(49) 7,7,9,9-tetramethyl-2-ethyl-1-oxa-3-oxo-4-(2,3-epoxypropyl)-4,8-diazaspiro-(4,5)-decane
(50) 7,7,9,9-tetramethyl-2-pentyl-1-oxa-3-oxo-4-(2,3-epoxypropyl)-4,8-diazaspiro-(4,5)-decane
(51) 7,7,9,9-tetramethyl-2-iso-pentyl-1-oxa-3-oxo-4-(2,3-epoxypropyl)-4,8-diazaspiro-(4,5)-decane
(52) 7,7,9,9-tetramethyl-2-isoheptyl-1-oxa-3-oxo-4-(2,3-epoxypropyl)-4,8-diazaspiro-(4,5)-decane
(53) 2,2,4,4-tetramethyl-7-oxa-3,14-diaza-14-(2,3-epoxypropyl)-13-oxodispiro-(5,1,4,2)-tetradecane
(54) 2,2,4,4-tetramethyl-7-oxa-3,15-diaza-15-(2,3-epoxypropyl)-14-oxodispiro-(5,1,5,2)-pentadecane
(55) 2,2,4,4-tetramethyl-7-oxa-3,12-diaza-21-(2,3-epoxypropyl)-20-oxodispiro-(5,1,5,2)-heneicosane
(56) 2,2,4,4,10,10,12,12-octamethyl-7-oxa-3,11,14-triaza-14-(2,3-epoxypropyl)-15-oxodispiro-(5,1,5,2)-pentadecane
(57) 7,7,9,9-tetramethyl-1-oxa-2-(2,4-dichlorophenyl)-3-(2,3-epoxypropyl)-3,8-diaza-4-oxospiro-(4,5)-decane.

The new compuonds in which n=1 are obtained by nucleophilic substitution of the halogen atom in an epihalogenohydrin of the formula (V), halogen being understood as meaning a chlorine, bromine or iodine atom, preferably chlorine, by polyalkyloxadiazaspirodecanes of the formula (IV) in accordance with the following equation, with elimination of hydrogen halide. Subsequent heating of the oxirane leads to the formation of polyethers in which n>1.

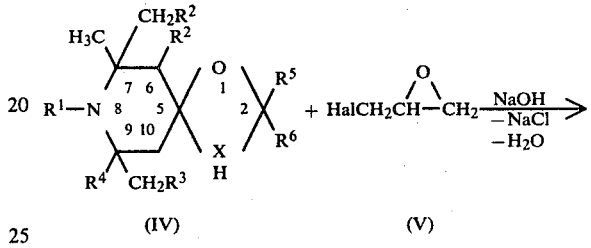

(IV)     (V)

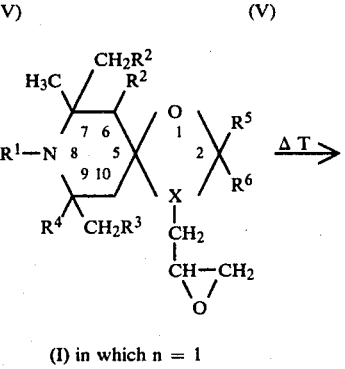

(I) in which n = 1

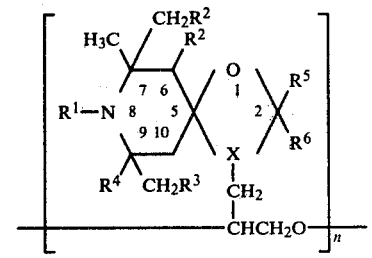

(I) in which 1 < n < 50

In the formulae of the equation, the radicals $R^1$, $R^2$, $R^3$, $R^4$, $R^5$, $R^6$, X, Hal and n have the meansing indicated above.

The compounds in which n=1 are synthesized by reacting the educts (IV) and (V), in a molar ratio of 1:1 to 1:5, preferably 1:1 to 1:2 and especially 1:1 to 1:1.2, in an inert organic solvent in the presence of an equimolar to twenty-fold molar quantity of solid alkali metal hydroxide or the corresponding quantity of a 20% to 50% strength aqueous solution of an alkali metal hydroxide, using a phase transfer catalyst. The reaction temperature is 20° to 120°, preferably 20° to 80° and especially 40° to 60° C.

Suitable organic solvents are aliphatic or aromatic hydrocarbons, such as, for example, petroleum ether, hexane, heptane, gasoline fractions, toluene, cyclohexane, xylene or the like.

Phase transfer catalysts are understood as meaning substances belonging to the group comprising quaternary ammonium halides. Tricaprylmethylammonium chloride is particularly suitable. 0.1 to 5% by weight, relative to the compound (IV), is required.

In general, the reaction is complete after one to 20 hours.

The compounds in which n=1 are isolated by separating the phases, if appropriate after adding a little water. The organic phase is washed several times with water, dried over $Na_2SO_4$ or $MgSO_4$ and concentrated. In the majority of cases oily products result.

Solid, amorphous polyethers, initially produced in the form of a glass, having $1 < n < 50$ can be obtained from the epoxides obtained in this manner, by heating the latter at 100° to 240°, preferably 100° to 200° and especially 120° to 180° C. Low degrees of polymerization can be achieved by a brief polymerization period and high degrees of polymerization can be achieved by a long period of polymerization. A tendency towards higher degrees of polymerization is similary observed at increased temperatures.

The polymers or oligomers can also be prepared by following a procedure in which the epoxides are not first isolated at all, but the whole reaction mixture, after the epichlorohydrin has been reacted with the azaspirodecane, is raised to the higher temperatures mentioned and is worked up after polymerization has been effected.

Since water is always present in the polymerization, the end groups of the polymers are probably —H and —OH.

The polyalkyloxadiazaspirodecanes used as the starting materials are known and are accessible by the instructions quoted in German Offenlegungsschriften Nos. 2,606,026, 2,634,957 and 2,834,962.

That the reaction should proceed in the manner observed is surprising and was not to be foreseen. Particularly in the case of educts (IV) in which $R^1$=H, it would not have been expected at all that the nucleophilic attack on the epihalogenohydrin would take place exclusively at the amide nitrogen (position 3 or 4 of the ring system). It would, on the contrary, have been necessary to assume that the basic amino nitrogen of the piperidine ring, which has considerably stronger nucleophilic properties, would react with the epihalogenohydrin.

The fact that it is possible to polymerize the oxiranes obtained as primary products (compounds I in which n=1) to give polyethers could also not have been foreseen, since, in principle, a polyaddition reaction resulting from the amine nitrogen (position 8 of the ring system I) adding on to the epoxy group also seems possible.

High-molecular polyalkylpiperidine stabilizers are already known. However, in contrast with the new polyesters obtained by polymerization, these are addition and condensation polymers containing polyalkylpiperidine radicals (German Offenlegungsschrift No. 2,719,131 and Published European Application No. 1,835, 2,005 and 769). Of these polymeric stabilizers, the product from Published European Application No. 769, which is obtained by an intermolecular polyaddition reaction of the substance according to Example 2 of German Offenlegungsschrift No. 2,233,122, that is to say 3-(2,3-epoxypropyl)-7,7,9,9-tetramethyl1,3,8-triazaspiro-(4,5)-decane-2,4-dione, belongs to the state of the art which is nearest to the present invention. Under identical test conditions, the quoted product according to Example 2 of German Offenlegungsschrift No. 2,233,122 is very much less effective than the product according to Example 58 of German Offenlegungsschrift No. 2,227,689, which should also be included in the nearest state of the art (the stability of polypropylene together with the substance according to Example 2 is 750 hours and with the substance according to Example 58 is 1,420 hours). In the applied technology tests carried out within the scope of the present invention, the product according to German Offenlegungsschrift No. 2,227,689 has therefore been employed as the comparison substance.

The said polymeric stabilizers hitherto known suffer from the drawback that they do not meet technical requirements in all the important parameters of applied technology, which include, besides effectiveness, volatility, resistance to migration (synonymous with low elutability) and heat stability. In contrast with this, the new stabilizers according to the invention fulfill these requirements in an excellent manner. They are very effective as stabilizers and, in spite of having a similar structure when compared with the stabilizer of the state of the art, described above, are substantially free from disadvantages stemming from physical properties.

The following examples are to be understood as plastics which can be protected from damage caused by the action of oxygen, heat and light:

Polymers which are derived from mono-unsaturated or di-unsaturated hydrocarbons, for example polyolefins, such as polyethylene, which can optionally be crosslinked, polypropylene, polybut-1-ene, polyisobutene, polymethylbut-1-ene, polymethylpent-1-ene, polyisoprene, polybutadiene, polystyrene, copolymers of the monomers on which the homopolymers mentioned are based, such as ethylenepropylene copolymers, propylene-but-1-ene copolymers, propylene-isobutene copolymers and styrene-butadiene copolymers and also terpolymers of ethylene and propylene with a diene, such as, for example, hexadiene, dicyclopentadiene or ethylidenenorbornene; mixtures of the abovementioned homopolymers, such as, for example, mixtures of polypropylene and polyethylene, polypropylene and polybut-1-ene, polypropylene and polyisobutylene or butadiene-acrylonitrile copolymers containing a styrene-butadiene copolymer.

Halogen-containing vinyl polymers, such as polyvinyl chloride, polyvinylidene chloride, polyvinyl fluoride, polychloroprene and chlorinated rubbers, and also copolymers of vinyl chloride and vinylidene chloride with one another and with other olefinically unsaturated monomers.

Polymers which are derived from $\alpha,\beta$-unsaturated acids and derivatives thereof, such as polyacrylates and polymethacrylates, polyacrylamides and polyacrylonitrile and also copolymers thereof with one another and with other vinyl compounds, such as acrylonitrile/butadiene/styrene, acrylonitrile/styrene and acrylonitrile/styrene/acrylic ester copolymers.

Polymers which are derived from unsaturated alcohols and amines or acyl derivatives or acetals thereof, such as polyvinyl alcohol, polyvinyl acetate, stearate, benzoate or maleate, polyvinyl butyral, polyallyl phthalate and polyallyl melamine and copolymers thereof with other vinyl compounds, such as ethylene/vinyl acetate copolymers.

Monomers and copolymers which are derived from epoxides, such as polyethylene oxide, or polymers which are derived from bisglycidyl ethers.

Polyacetals, such as polyoxymethylene and polyoxyethylene, and also polyoxymethylenes which contain ethylene oxide as the comonomer.

Polyurethanes and polyureas.

Polycarbonates.

Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

Polyesters which are derived from dicarboxylic acids and dialcohols and/or from hydroxycarboxylic acids or the corresponding lactones, such as polyethylene terephthalate, polybutylene terephthalate and poly-1,4-dimethylolcyclohexane terephthalate.

Crosslinked polymers which are derived from aldehydes on the one hand and from phenols, ureas and melamines on the other hand, such as phenol-formaldehyde resins, urea-formaldehyde resins and melamine-formaldehyde resins.

The stabilization of polyolefins, styrene polymers, polyamides, poly(meth-)acrylates and polyurethanes is particularly important. Examples of these are high-density and low-density polyethylene, polypropylene, ethylene-propylene copolymers, polystyrene, styrene-butadiene-acrylonitrile tercopolymers, mixtures of polyolefins or of styrene polymers and polyurethanes based on polyethers or polyesters in the form of lacquers, filaments, sheets, panels, films, elastomers or foams.

The new stabilizers are incorporated into the polymer compositions in accordance with methods which are generally customary. The incorporation can be effected, for example, by mixing the compounds, and optionally further additives, into the melts before or during the shaping process, or by applying the dissolved or dispersed compounds to the polymer directly or by mixing them into a solution, suspension or emulsion of the polymer, if appropriate subsequently allowing the solvent to evaporate. The quantities to be added to the plastics are 0.05 to 5, preferably 0.1 to 2.5 and especially 0.1 to 1.0, % by weight, relative to the material to be stabilized.

The new compounds can also be added to the plastics to be stabilized in the form of a master batch containing these compounds, for example, in a concentration of 2.5 to 50, preferably 5.0 to 20, % by weight.

The plastics to be stabilized can, if appropriate, also contain other known and conventional additives. Examples of the latter which may be mentioned are antioxidants based on phenols and sulfides, UV absorbers and light stabilizers, phosphite stabilizers, metal compounds, epoxy stabilizers and polyhydric alcohols.

Examples of suitable antioxidants are sterically hindered phenols, such as 4,4'-butylidene-bis-(2,6-ditert.-butylphenol), 4,4'-thio-bis-(2-tert.-butyl-5-methylphenol), phenolic triazine compounds, thiodipropionic acid esters of fatty alcohols and dioctadecyl sulfide and disulfide.

The UV absorbers and light stabilizers include, for example, 2-(2'-hydroxyphenyl)-benztriazoles, such as 2-(2'-hydroxy-5'-methylphenyl)-benztriazole, 2-hydroxybenzophenones, such as 2-hydroxy-4-octoxybenzophenone, stabilizers belonging to the group of the salicylates, such as octylphenyl salicylate, nickel chelates, oxamides and sterically hindered piperidine compounds.

Phosphites which should be mentioned are trisnonylphenyl phosphite, trislauryl phosphite or esters of pentaerythritol phosphite.

The following are understood in this connection as metal compounds which are known as stabilizers: calcium, zinc, barium, strontium, cadmium, magnesium, aluminum and lead soaps of aliphatic carboxylic acids or hydroxycarboxylic acids having about 12 to 32 C atoms, salts of the said metals with aromatic carboxylic acids, such as benzoates or salicylates, and also (alkyl)-phenates of these metals, and also organo-tin compounds, such as, for example, dialkyl-tin thioglycolates and carboxylates.

Examples of known epoxy stabilizers are epoxidized higher fatty acids, such as epoxidized soya bean oil, tall oil or linseed oil or epoxidized butyl oleate, and also epoxides of long-chain olefins. Polyhydric alcohols can be, for example, pentaerythritol, trimethylolpropane, sorbitol or mannitol, that is to say preferably alcohols having 5 or 6 C atoms and 2 to 6 OH groups.

An effective combination of stabilizers for poly-$\alpha$-olefins, such as, for example, high-pressure, medium-pressure and low-pressure polymers of $C_2$- to $C_4$-$\alpha$-olefins, especially polyethylene and polypropylene, or copolymers of such $\alpha$-olefins, consists, relative to 100 parts by weight of polymer, of, for example, 0.01 to 5 parts by weight of one of the compounds to be used in accordance with the invention, 0.05 to 5 parts by weight of a phenolic stabilizer, optionally 0.01 to 5 parts by weight of a sulfur-containing co-stabilizer and optionally 0.01 to 3 parts by weight of a basic or neutral metal soap, such as, for example, calcium stearate or zinc stearate, and optionally 0.1 to 5 parts by weight of a phosphite and optionally 0.01 to 5 parts by weight of a known UV stabilizer belonging to the group consisting of alkoxyhydroxybenzophenones, 4-hydroxyphenyl-benztriazoles, benzylidenemalonic acid mononitrile-ester or the so-called quenchers, such as, for example, nickel chelates.

The plastics which have been stabilized in accordance with the invention can be used in various forms, for example, as films, fibers, tapes or profiles or as binders for lacquers, adhesives or putties.

The following Examples serve to illustrate the subject of the invention in greater detail.

EXAMPLE 1

2,2,7,7,9,9-Hexamethyl-1-oxa-3-(2,3-epoxypropyl)-3,8-diaza-4-oxospiro-(4,5)-decane and the oligomer obtained therefrom.

24.0 g (0.1 mole) of 2,2,7,7,9,9-hexamethyl-1-oxa-3,8-diaza-4-oxospiro-(4,5)-decane, 18.5 g (0.2 mole) of epichlorohydrin, 5 drops of tricaprylmethylammonium chloride (® Aliquat 336 made by Messrs. Fluka) and 40 g of 50% strength sodium hydroxide solution ($\triangleq$ 0.5 mole of NaOH) were added successively to 150 ml of toluene, after which the reaction mixture was stirred at 65° C. for 16 hours. When the stirrer had been switched off, two clear phases were formed and these were separated. The organic phase was washed with three times 50 ml of water, dried over 50 g of sodium sulfate, stirred at room temperature for 30 minutes with 1 g of active charcoal and filtered. The volatile constituents were removed in vacuo. The residue was a colorless oil which is the epoxy compound indicated in the title. It was heated at 170° C. for three hours and, in the course thereof, polymerized to give a solid, colorless resin with a melting point of 130° to 184° C. The relative specific viscosity (RSV value) at 25° C. in a 1% strength by weight solution in toluene was 0.03.

EXAMPLES 2 to 44

The reaction was carried out as indicated in Example 1. The Table below lists the experimental conditions and data on the monomeric and polymeric products of the process. Column 2 ("Compound No.") refers to the list of typical monomeric process products in the description pages 4 to 8, from which also follows the particular polyalkyldiazaspirodecane employed.

| Stabilizer according to Example | Loss in weight in mg/cm² on reaching ... °C. | | | |
|---|---|---|---|---|
| | 220 | 260 | 300 | 10 minutes at 300 |
| 1 | 0.32 | 0.63 | 3.16 | 9.80 |
| 2 | 0.16 | 2.21 | 6.64 | 16.91 |
| 6 | 0.16 | 0.47 | 1.42 | 3.63 |
| 7 | 0.32 | 1.26 | 4.27 | 9.48 |
| 8 | 0.16 | 0.47 | 2.05 | 7.74 |
| 9 | 0.16 | 0.63 | 2.53 | 9.01 |
| 17 | 0.16 | 0.47 | 2.21 | 8.37 |
| 21 | 0.32 | 0.79 | 2.21 | 5.37 |
| 22 | 0.00 | 0.16 | 1.74 | 4.58 |

| Example No. | Compound No. | Preparation of the epoxy compound | | Mp. of the epoxy compound (°C.) | Polymerization | | Polymer | |
|---|---|---|---|---|---|---|---|---|
| | | time (hours) | temp.(°C.) | | time (hours) | temp.(°C.) | Mp.(°C.) | RSV value |
| 2 | 2 | 15 | 60 | 175 | 6 | 170 | 142–183 | 0.02 |
| 3 | 4 | 10 | 60 | Oil | 6 | 150 | 56–88 | 0.05 |
| 4 | 5 | 16 | 50 | Oil | 6 | 170 | 59–92 | 0.03 |
| 5 | 6 | 9 | 60 | Oil | 3 | 175 | 102–154 | 0.02 |
| 6 | 7 | 19 | 65 | Oil | 3 | 170 | 99–171 | 0.02 |
| 7 | 7 | 19 | 65 | Oil | 6 | 170 | 140–196 | 0.02 |
| 8 | 9 | 15 | 70 | Oil | 3 | 170 | 100–149 | 0.02 |
| 9 | 9 | 15 | 70 | Oil | 6 | 170 | 134–188 | 0.02 |
| 10 | 10 | 20 | 57 | Oil | 6 | 150 | 84–138 | 0.03 |
| 11 | 11 | 13 | 60 | Oil | 1 | 200 | 95–121 | 0.02 |
| 12 | 12 | 7 | 66 | Oil | 5 | 180 | 98–161 | 0.03 |
| 13 | 13 | 11 | 60 | Oil | 5 | 170 | 91–141 | 0.04 |
| 14 | 14 | 15 | 60 | Oil | 1 | 200 | 55–128 | 0.02 |
| 15 | 45 | 15 | 60 | Oil | 5 | 170 | 80–119 | 0.03 |
| 16 | 54 | 13 | 55 | 95–99 | 5 | 170 | 168–229 | 0.02 |
| 17 | 1 | 16 | 65 | Oil | 6 | 170 | 151–208 | 0.04 |
| 18 | 56 | 18 | 50 | 165 | 6 | 170 | 55–191 | 0.03 |
| 19 | 19 | 15 | 60 | Oil | 6 | 180 | 128–149 | 0.04 |
| 20 | 20 | 15 | 50 | Oil | 6 | 150 | 74–117 | 0.02 |
| 21 | 21 | 16 | 55 | Oil | 3 | 170 | 86–139 | 0.02 |
| 22 | 21 | 16 | 55 | Oil | 6 | 170 | 148–201 | 0.02 |
| 23 | 23 | 14 | 60 | Oil | 6 | 150 | 105–137 | 0.02 |
| 24 | 24 | 3 | 60 | Oil | 3 | 180 | 84–134 | 0.03 |
| 25 | 25 | 16 | 65 | Oil | 6 | 150 | 66–103 | 0.02 |
| 26 | 26 | 20 | 60 | Oil | 5 | 170 | 60–116 | 0.03 |
| 27 | 27 | 8 | 50 | Oil | 3 | 150 | 72–124 | 0.03 |
| 28 | 28 | 14 | 40 | Oil | 3 | 150 | 57–94 | 0.03 |
| 29 | 29 | 14 | 60 | Oil | 6 | 180 | 144–170 | 0.03 |
| 30 | 42 | 13 | 50 | Oil | 6 | 170 | 72–96 | 0.03 |
| 31 | 30 | 16 | 60 | Oil | 1 | 200 | 123–176 | 0.02 |
| 32 | 37 | 14 | 70 | Oil | 1.5 | 190 | 138–189 | 0.02 |
| 33 | 37 | 14 | 70 | Oil | 3 | 170 | 131–174 | 0.02 |
| 34 | 38 | 8 | 55 | Oil | 3 | 170 | 136–198 | 0.02 |
| 35 | 39 | 15 | 60 | Oil | 3 | 170 | 138–190 | 0.01 |
| 36 | 39 | 15 | 60 | Oil | 6 | 170 | 172–247 | 0.03 |
| 37 | 40 | 13 | 50 | Oil | 6 | 170 | 65–84 | 0.02 |
| 38 | 41 | 14 | 50 | Oil | 1 | 200 | 129–166 | 0.01 |
| 39 | 42 | 13 | 50 | Oil | 6 | 170 | 72–96 | 0.03 |
| 40 | 43 | 6 | 50 | 138 | 3 | 170 | 101–163 | 0.02 |
| 41 | 43 | 12 | 60 | Oil | 6 | 170 | 129–177 | 0.03 |
| 42 | 50 | 14 | 55 | Oil | 6 | 170 | 57–78 | 0.02 |
| 43 | 51 | 9 | 60 | Oil | 6 | 170 | 78–111 | 0.03 |
| 44 | 57 | 20 | 50 | Oil | 6 | 170 | 58–86 | 0.04 |

EXAMPLE 45

This Example shows the volatility of the new stabilizers compared with the products of German Offenlegungsschrift No. 2,227,689.

The volatilities were determined in an apparatus for thermogravimetric analysis. For this, equal quantities (500 mg) of the substances according to the invention and of the comparison substances were heated in an atmosphere of nitrogen up to 300° C. at a rate of 2 K/minute and the loss of substance in mg/cm² was measured. The following Table shows the results:

| 32 | 0.00 | 0.47 | 4.27 | 11.69 |
| 33 | 0.00 | 0.36 | 6.64 | 17.22 |
| 35 | 0.00 | 0.16 | 0.95 | 3.48 |
| 36 | 0.00 | 0.32 | 1.26 | 3.79 |
| 40 | 0.32 | 1.26 | 2.84 | 7.90 |
| 40 (Monomer) | 0.48 | 2.25 | 3.00 | 7.11 |
| 41 | 0.16 | 0.47 | 1.90 | 6.64 |
| Comparison+ | 14.06 | 45.82 | 148.52 | 153.26 |

+Example 58 of German Offenlegungsschrift 2,227,689

EXAMPLE 46

The following procedure was followed in order to demonstrate the stabilizing properties of the new compounds:

100 parts by weight of polypropylene having a melt index is of approx. 6 g/10 minutes (determined as specified in ASTM D 1238-62 T) and a density of 0.90 were mixed with 0.1 part by weight of pentaerythritol tetrakis-3-(3,5-di-tert.-butyl-4-hydroxyphenyl)-propionate, 0.2 part by weight of calcium stearate and 0.3 part by weight of the stabilizer, according to the invention, to be tested.

In order to achieve as uniform a distribution as possible on the polymer grains, the stabilizers were dissolved in a solvent. The solution was added dropwise to the polypropylene powder, while stirring, the bulk of the solvent being re-vaporized by simultaneous irradiation with an IR lamp. After approx. 20 minutes the calcium stearate was added and mixing was continued for a further 10 minutes. Solvent residues were removed by drying at 50° C. for 120 minutes in a drying cabinet.

The polypropylene was injection molded at 240° C. on a type SP 50 Windsor injection molding machine to give 60×60×1 mm sheets. Test specimens were punched out of these sheets in accordance with DIN 53,455, Form 3, reduced in a scale of 1:3. The test specimens required as comparison samples were prepared analogously, but omitting the stabilizer to be tested and/or adding the comparison stabilizers.

The stability to light was determined by subjecting the samples to irradiation with alternating light in a Xenotest-1200 apparatus made by Original Hanau Quarzlampen GmbH. The intensity of the radiation was modulated by means of UV filters (special filter glass d=1.7 mm). The stability to light was tested as specified in DIN 53,387 (17 minutes moistening, 3 minutes sprinkling, black-body temperature 45° C. and atmospheric humidity 70 to 75%). The exposure time was measured in hours and the elongation at break was determined. The elongation at break was measured on a tensile testing machine made by Messrs. Instron, at a draw speed of 5 cm/minute.

| Stabilizer according to Example | Exposure time in hours | Measured elongation at break as % of initial value |
|---|---|---|
| 2 | 1 100 | >50 |
| 8 | 1 100 | >50 |
| 22 | 1 100 | >50 |
| 35 | 1 100 | >50 |
| 41 | 1 100 | >50 |
| 54 | 1 100 | >50 |
| Polypropylene Comparison without stabilizer | 260 | 1 |
| Comparison+ | 320 | 1 |
| | 1 100 | 2 |

+Compound according to Example 58 of German Offenlegungsschrift 2,227,689

EXAMPLE 47

0.26 part by weight of the stabilizers indicated below are mixed into polypropylene (Hostalen PPU VP 1770 F of HOECHST AG) with a melt flow-index MFI of 190/51.9/10 minutes, see DIN 53,535, via a high-speed laboratory mixer. The material thus stabilized was melted under the customary processing conditions in a laboratory extruder and processed via a spinning pump having a multiple spinning head to give monofilaments (87 dtex) which were subsequently stretched in a ratio of 1:2.5. Groups of 24 of these filaments were texturized to form yarn and the latter was processed to give test fabrics. These specimens were subjected to a light fastness test in a Fadeometer and, after the exposure time indicated, were subjected to the fingernail test (rubbing the thumbnail gently over the fabric). The degree of degradation is expressed in ratings, 0 denoting no damage and 1 to 5 denoting increasing destructibility.

| Stabilizer according to Example | Destructibility of the fabric after ... hours Exposure time | | |
|---|---|---|---|
| | 40 | 80 | 160 |
| no stabilizer (comparison) | 0 | 0 | 5 |
| 21 | 0 | 0 | 0 |
| 41 | 0 | 0 | 0 |
| Comparison+ | 0 | 0 | 1 |

+Stabilizer according to Example 58 of German Offenlegungsschrift 2,227,689

We claim:
1. An ether or epoxide, containing polyalkylpiperidine groups, of the formula (I)

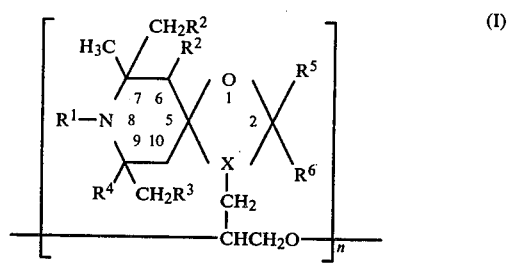

in which n is an integer from 1 to 50, when n equals 1, an oxirane ring being completed via the free bonds, X denotes a group of the formula (II) or (III)

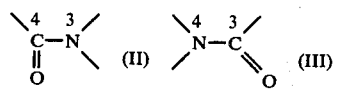

wherein the indices 3 and 4 indicate the ring positions in the diazaspirodecane system and one bond of the nitrogen is attached to the $CH_2$ group of the ether radial, $R^1$ is hydrogen, oxygen or $C_1$- to $C_{12}$-alkyl, $R^2$ and $R^3$ are either identical and denote hydrogen or a $C_1$- to $C_5$-alkyl group, in which case $R^4$ is a methyl group, or $R^2$ is hydrogen or $C_1$- to $C_5$-alkyl and $R^3$ and $R^4$, conjointly with the carbon atoms to which they are linked, represent a $C_5$- or $C_6$-cycloalkyl group or a group of the formula

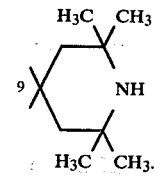

$R^5$ and $R^6$ are identical or different and represent hydrogen, $C_1$- to $C_{30}$-alkyl, a phenyl or naphthyl grop which is unsubstituted or substituted by chlorine or $C_1$- to $C_4$-alkyl, or a $C_7$- to $C_{12}$-phenylalkyl group which is unsubstituted or substituted by $C_1$- to $C_4$-alkyl, or $R^5$ and $R^6$, conjointly with the carbon atom which is linked to them, denote a $C_5$- to $C_{18}$-cycloalkyl group which is unsubstituted or substituted by up to four $C_1$- to $C_4$-alkyl groups, or denote a group of the formula

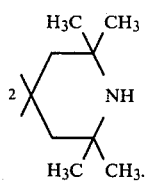

2. A process for the preparation of compounds as claimed in claim 1, which comprises reacting a polyalkyl-1-oxadiazaspirodecane of the formula (IV)

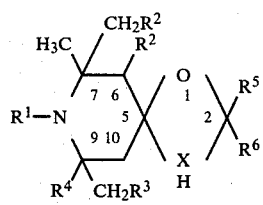

in which $R^1$, $R^2$, $R^3$, $R^4$, $R^5$, $R^6$ and X have the meanings indicated in claim 1, with an epihalogenohydrin in a molar ratio of 1:1 to 1:5 in a two-phase system consisting of an organic solvent and an alkali metal hydroxide in the solid form or as an aqueous solution, in the presence of a phase transfer catalyst at 20° to 120° C., after which the resulting oxiranes are polymerized at 70° to 240° C. to give the ethers in which n=2 to 50.

3. A process as claimed in claim 2, wherein the phase transfer catalyst is a quaternary ammonium halide.

4. A process for stabilizing synthetic polymers against the harmful effect of light, which comprises adding to the polymers, if appropriate together with previously known stabilizing substances, 0.01 to 5 parts by weight, relative to the polymer, of a stabilizer as claimed in claim 1.

5. The process of claim 4, wherein the polymer is a polyolefin.

6. The process of claim 4, wherein the polymer is a halogen-containing polymer.

7. The process of claim 4, wherein the polymer is a polyacrylate or polymethacrylate.

8. The process of claim 4, wherein the polymer is a homopolymer or copolymer of polystyrene.

9. Synthetic polymers which have been stabilized against UV decomposition and which contain 0.01 to 5 parts by weight, relative to the polymer, of a stabilizer as claimed in claim 1.

10. A compound according to claim 1 having the structural formula

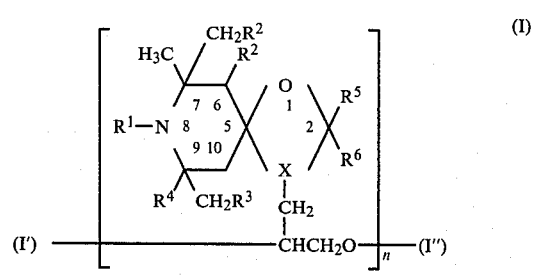

wherein n is an integer >1, but less than 50, X, $R^1$, $R^2$, $R^3$, $R^4$, $R^5$, and $R^6$ are as defined in claim 1, and (I') and (I'') are polyether end groups which are residues from the polymerization of the epoxide which is the compound of formula (I) when n=1.

11. A compound according to claim 10 wherein said polyether end groups result from the reaction of said epoxide with water.

12. A compound according to claim 10 which is a 2-R, 2-R, 6-CH R, 7-methyl, 7-CH R, 9,9-polyalkyl-3-(2,3-epoxypropyl)-1-oxa-3,8-diaza-4-oxospiro-(4,5)-decane, or a 2-$R^5$, 2-$R^6$, 7-methyl, 7-$CH_2R^2$, 9,9-polyalkyl-4-(2,3-epoxypropyl)-1-oxa-3-oxo-4,8-diazaspiro-(4,5)-decane, or a polyether of said formula (I) derived therefrom, wherein $R^2$, $R^5$, and $R^6$ are as defined previously.

13. A compound according to claim 10 wherein $R^3$ is hydrogen or a $C_1$-$C_5$-alkyl group and $R^4$ is a methyl group.

* * * * *